(12) United States Patent
Prentice et al.

(10) Patent No.: US 8,840,784 B2
(45) Date of Patent: Sep. 23, 2014

(54) DEVICE FOR HOLDING A COLUMN OR CARTRIDGE IN PROXIMITY TO A DETECTOR AND METHODS OF USING THE SAME

(75) Inventors: David P. Prentice, Millville, MA (US); Theodore C. Ciolkosz, Milton, MA (US); Joseph D. Antocci, Leominster, MA (US)

(73) Assignee: Waters Technologies Corporation, Milford, MA (US)

( * ) Notice: Subject to any disclaimer, the term of this patent is extended or adjusted under 35 U.S.C. 154(b) by 2335 days.

(21) Appl. No.: 10/598,313

(22) PCT Filed: Mar. 2, 2005

(86) PCT No.: PCT/US2005/006707
§ 371 (c)(1),
(2), (4) Date: Jun. 25, 2008

(87) PCT Pub. No.: WO2005/092467
PCT Pub. Date: Oct. 6, 2005

(65) Prior Publication Data
US 2008/0277345 A1 Nov. 13, 2008

Related U.S. Application Data

(60) Provisional application No. 60/550,970, filed on Mar. 5, 2004.

(51) Int. Cl.
*G01N 30/62* (2006.01)
*G01N 30/60* (2006.01)
*G01N 30/30* (2006.01)

(52) U.S. Cl.
CPC ........ *G01N 30/6047* (2013.01); *G01N 30/6091* (2013.01); *G01N 2030/3007* (2013.01); *G01N 2030/3084* (2013.01); *G01N 30/62* (2013.01)
USPC ...................................... 210/198.2; 210/656

(58) Field of Classification Search
CPC .......... G01N 30/6047; G01N 30/6091; G01N 30/62; G01N 2030/3084; G01N 2030/3007
USPC .......... 210/198.2, 656, 232, 236, 238; 96/101
See application file for complete search history.

(56) References Cited

U.S. PATENT DOCUMENTS 3,263,811 A * 8/1966 Baker et al. .................... 210/136
3,994,805 A * 11/1976 Ito ................................. 210/635

(Continued)

FOREIGN PATENT DOCUMENTS

JP      50150497 A    12/1975
JP      894537    3/1994

(Continued)

OTHER PUBLICATIONS

PTO 10-3836 translation of Japan Patent No. 2004093344 May 2010.*

(Continued)

*Primary Examiner* — Ernest G Therkorn
(74) *Attorney, Agent, or Firm* — Schmeiser, Olsen & Watts LLP

(57) ABSTRACT

Embodiments of the present invention are directed to methods and devices for minimizing band spreading of compositions separated by chromatographic processes. One embodiment of the present invention features a device (11) for holding a separation column or cartridge. The device (11) includes a housing (15) having a chamber for receiving one or more columns or cartridges. The columns and cartridges have an inlet for receiving fluid and an outlet for discharging fluid and a column axis corresponding generally with the flow of fluid from the inlet to the outlet. The columns and cartridges are suitable for performing separations in which a constant temperature is desirable. The housing (15) further includes a heating element for maintaining said chamber at a constant temperature. The device (11) further includes positioning means (17) for placing the column and cartridge outlet in proximity to a detector.

10 Claims, 3 Drawing Sheets

(56) References Cited

U.S. PATENT DOCUMENTS

| | | | |
|---|---|---|---|
| 4,019,372 A | 4/1977 | Parkell et al. | |
| 4,044,593 A * | 8/1977 | Haruki et al. | 73/23.25 |
| 4,051,025 A * | 9/1977 | Ito | 210/635 |
| 4,350,586 A * | 9/1982 | Conlon et al. | 210/149 |
| 4,451,365 A * | 5/1984 | Sattler et al. | 210/198.2 |
| 4,484,061 A * | 11/1984 | Zelinka et al. | 392/480 |
| 4,726,822 A * | 2/1988 | Cates et al. | 96/101 |
| 4,732,672 A * | 3/1988 | Kiang et al. | 210/198.2 |
| 4,966,695 A | 10/1990 | Joshua et al. | |
| 4,987,446 A * | 1/1991 | Mochimaru et al. | 399/113 |
| 5,021,162 A * | 6/1991 | Sakamoto et al. | 210/635 |
| 5,083,158 A * | 1/1992 | Kashima et al. | 399/114 |
| 5,169,521 A * | 12/1992 | Oka et al. | 210/198.2 |
| 5,238,557 A * | 8/1993 | Schneider et al. | 210/198.2 |
| 5,269,918 A * | 12/1993 | Lapidus et al. | 210/232 |
| 5,286,652 A * | 2/1994 | James et al. | 436/48 |
| 5,496,473 A * | 3/1996 | Chow | 210/635 |
| 5,559,283 A * | 9/1996 | Kaji et al. | 73/61.56 |
| 5,589,063 A * | 12/1996 | Sanford et al. | 210/198.2 |
| 5,646,048 A * | 7/1997 | Templin et al. | 436/180 |
| 5,794,103 A * | 8/1998 | Oh | 399/119 |
| 6,036,855 A * | 3/2000 | Shalon et al. | 210/198.2 |
| 6,294,088 B1 * | 9/2001 | Allington et al. | 210/198.2 |
| 7,536,792 B2 * | 5/2009 | Moore | 30/276 |
| 7,575,676 B2 * | 8/2009 | Prentice et al. | 210/198.2 |
| 7,688,485 B2 * | 3/2010 | Chen et al. | 358/502 |
| 2007/0221557 A1 * | 9/2007 | Barber et al. | 210/198.2 |

FOREIGN PATENT DOCUMENTS

| | | |
|---|---|---|
| JP | 920579 S | 2/1995 |
| JP | 20022267597 | 9/2002 |
| JP | 2002333438 A | 11/2002 |
| JP | 2004093344 | 3/2004 |

OTHER PUBLICATIONS

PTO Translation 14-4223 of Japan Patent No. 50150497 Jun. 2014.*
PTO Translation 14-4215 of Japan Patent No. 2002333438 Jun. 2014.*
English translation of Japanese Office Action in foreign counterpart application No. 2007-501926, dated Sep. 21, 2010.

* cited by examiner

DEVICE FOR HOLDING A COLUMN OR CARTRIDGE IN PROXIMITY TO A DETECTOR AND METHODS OF USING THE SAME

CROSS REFERENCE RELATED APPLICATION INFORMATION

This application is a 371 of PCT/US2005/006707, which, in turn, claims priority from U.S. Provisional Patent Application No. 60/550,970, filed Mar. 10, 2004. The contents of these applications are incorporated herein by reference.

FIELD OF THE INVENTION

The present invention relates to analytical instruments and methods of analysis.

BACKGROUND OF THE INVENTION

The present invention relates to methods and devices for minimizing band spreading caused by long tubing runs between a separation column or cartridge and a detector. Chemical analysis is a process in which the presence and/or quantity of a composition is determined. Chromatography is a process in which compositions are separated from each other, often used in chemical analysis. Typically, samples are in the form of a solution holding one or more compositions. A pump creates a flow of fluid. Samples are placed into this flow of fluid by a sample injector. The sample is carried by the flow of fluid through tubing to a column or cartridge. The cartridge or column is packed with a solid phase media. The different compounds held in the sample exhibit different affinities for the solid phase material and separate from each other. The flow from the column is received by a detector. The detector produces a signal that changes as the properties of the fluid changes takes place over time due to the separation of the compounds. These changes are recorded as peaks or bands and are indicative of a particular composition.

The separation of compound by the column or cartridge is reversible. The compositions leaving the solid phase media are able to redistribute and mix with the surrounding fluid. This redistribution of the concentrated compositions is known as band spreading. Band spreading is undesirable in that it tends to obscure compositions that are present in small concentrations.

Columns and cartridges are often contained in an assembly with sample injector functions and pumping functions. The assembly allows the environment of the column and cartridge to be controlled. The column and/or cartridge communicate with one or more detectors through runs of tubing. The long runs of tubing promote band spreading.

Placement of the column and/or cartridge in close proximity to the detector is difficult. The column or cartridge is then subjected to changes in temperature which may lead to shifts in peaks. Moving the column and/or cartridge to the detector, away from the sample injector, may cause mixing of the samples with each other.

SUMMARY OF THE INVENTION

Embodiments of the present invention are directed to methods and devices for minimizing band spreading of compositions separated by chromatographic processes. One embodiment of the present invention features a device for holding a separation column or cartridge. The device comprises a housing having a chamber for receiving one or more columns or cartridges. The columns and cartridges have an inlet for receiving fluid and an outlet for discharging fluid and an column axis corresponding generally with the flow of fluid from the inlet to the outlet. The columns and cartridges are suitable for performing separations in which a constant temperature is desirable. The housing further comprises a heating element for maintaining said chamber at a constant temperature. The device further comprises positioning means for placing the column and cartridge outlet in proximity to a detector.

As used herein the term "detector" means any instrument which produces a distinctive signal in the presence of a composition. The detector is preferably selected from the group of detectors consisting of mass spectrometers; optical detectors, such as photodiode array detectors, ramon light scattering detectors, absorbance detectors, fluorescence detectors, refractometers, electro-chemical detectors, viscosity detectors and the like.

Preferably, the columns and cartridges receive sample from a sample injector and a fluid from a pump. A common sample injector is an autosampler. An autosampler is a apparatus for receiving samples in one or more vials or containment vessels and withdrawing aliquots of such samples. The aliquots are injected into the flow from a pump in a automatic manner. This application will use the term sample injector to encompass manual sample injectors and automatic sample injectors, i.e. autosamplers.

The positioning means comprises an arm, slide, linkage or hinge. The arm, slide, linkage or hinge are capable of movement and positioning to allow the housing to be placed with the outlet of a column or cartridge proximal to the inlet of the detector. The short distance spanning the outlet of the column and/or cartridge to the inlet of the detector is, preferably, spanned by a relatively short tube or conduit. The shorter distance improves the sensitivity of the detector, pump and sample injector combination by reducing band spreading. For example, in one embodiment where the positioning means comprises a hinge, the hinge is affixed to the pump or sample injector apparatus and the housing is swung to a position in which the outlet of the column is close to the inlet of the detector.

Preferably the first housing has a cradle. The cradle has a cradle axis of rotation substantially aligned parallel with said column axis. The cradle has a cradle opening for receiving columns and cartridges. The cradle opening has an open position and a closed position. The opening is shut upon the cradle assuming the closed position to provide a temperature controlled environment for the column or cartridge. In the open position, the opening is accessible to receive and remove columns and cartridges.

Preferably, the heating element is contained in the cradle. One preferred heating element is electrical resistance circuits.

Preferably, device is part of an assembly of a pump, sample injector or combined modules of pumps and sample injector. Thus, the device of the present invention is convenient for use and promotes laboratory bench organization.

A further embodiment of the present invention features a method of minimizing band spreading in separation processes. The method comprising the steps of providing a first housing having a chamber for receiving one or more columns or cartridges. The columns and cartridges have an inlet for receiving fluid and an outlet for discharging fluid and an column axis corresponding generally with the flow of fluid from the inlet to the outlet. The column and cartridges are for performing separations such as liquid chromatography. The housing has a heating element for maintaining the chamber at a constant temperature. The method further comprises the step of providing positioning means for placing the column and cartridge outlet in proximity to a detector to allow connection to a detector. The method comprises the step of placing the housing in proximity to the detector with the positioning means to minimize tubing spanning from the column outlet to the detector and minimize band spreading.

Preferably, the method further comprises the step of providing a device wherein the first housing has a cradle having an opening. The cradle has a cradle axis of rotation substantially aligned parallel with the column axis. The cradle rotates between an open position and a closed position. In the open position, the cradle opening is accessible for receiving columns and cartridges. The opening is shut upon the cradle assuming the closed position to provide a controlled environment for the column and/cartridge. The method further comprising the steps of rotating the cradle to the open position to receive a column or cartridge. Next, rotating the cradle to assume the closed position, and positioning the column or cartridge in proximity to the detector.

Preferably, the positioning means is an arm, linkage, slide or hinge. The positioning element is preferably attached to apparatus selected from the group consisting of a pump, sample injector or a combined module a of pump and sample injector. One preferred positioning means is a hinge affixed to the housing and the injector or pump. The housing rotated or pivots to allow positioning close to a detector.

Preferable the method further comprises the step of providing a heating element contained in said cradle. The method further comprises the step of heating the cradle to a constant temperature.

These and other features and advantages will be apparent to individuals skilled in the art upon reference to the figures and detailed description that follow.

DETAILED DESCRIPTION OF THE INVENTION

The present invention will be described in detail with respect to methods and devices for minimizing band spreading of compositions separated by chromatographic processes. However, individuals skilled in the art will recognize that aspects of the present invention have broader application can be used wherever it is desirable to place a separation device such as a column or cartridge close to a further instrument.

Figure 1:
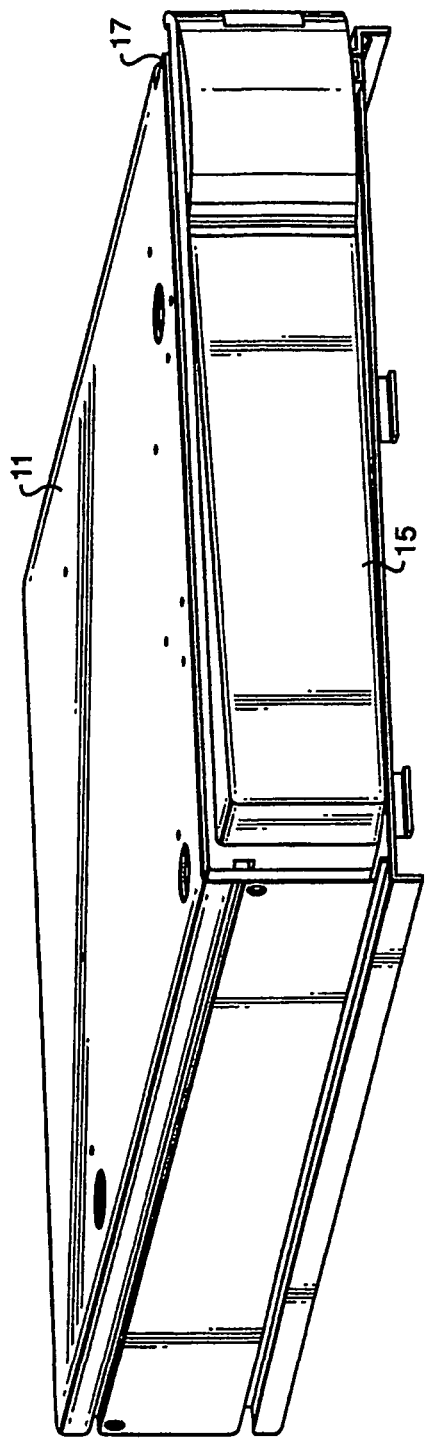
FIG. 1 depicts a device embodying features of the present invention.
Figure 2:
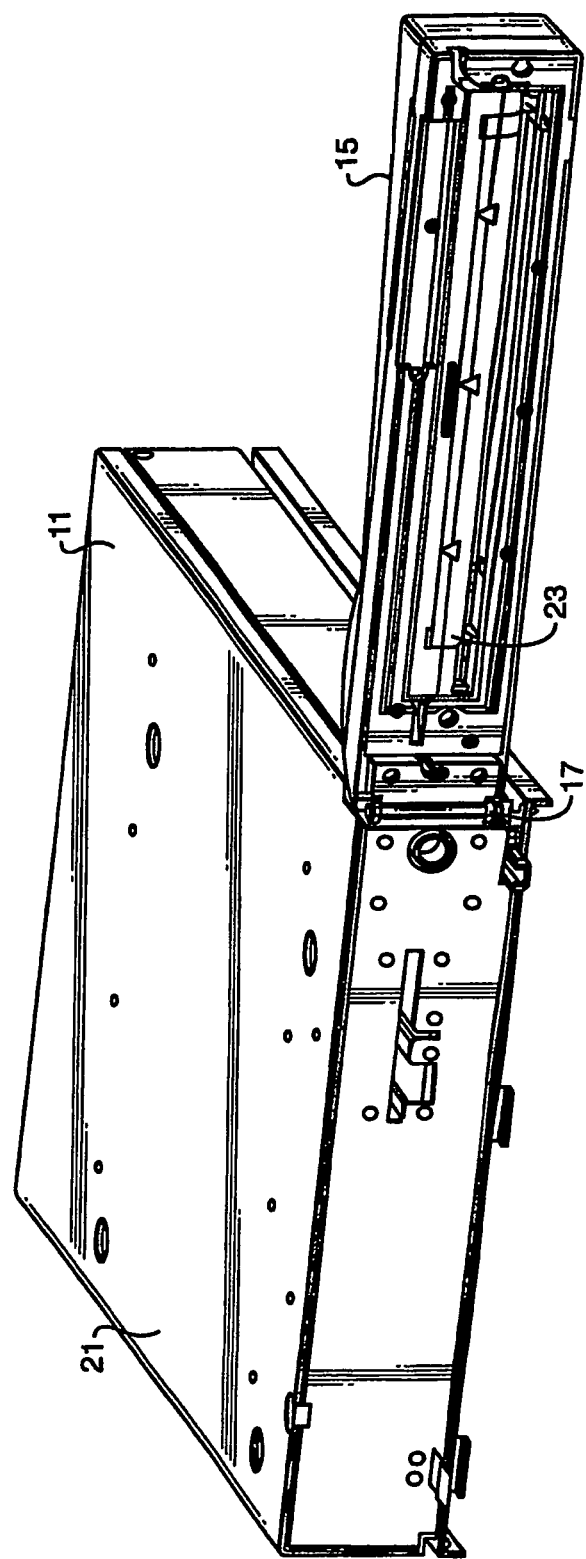
FIG. 2 depicts the device positioned to cooperate with a detector.

One embodiment of the present invention a device for holding a separation column or cartridge, generally designated by the numeral 11, is depicted in FIGS. 1 and 2. The device 11 comprises a housing 15 and positioning means 17.

Figure 3:
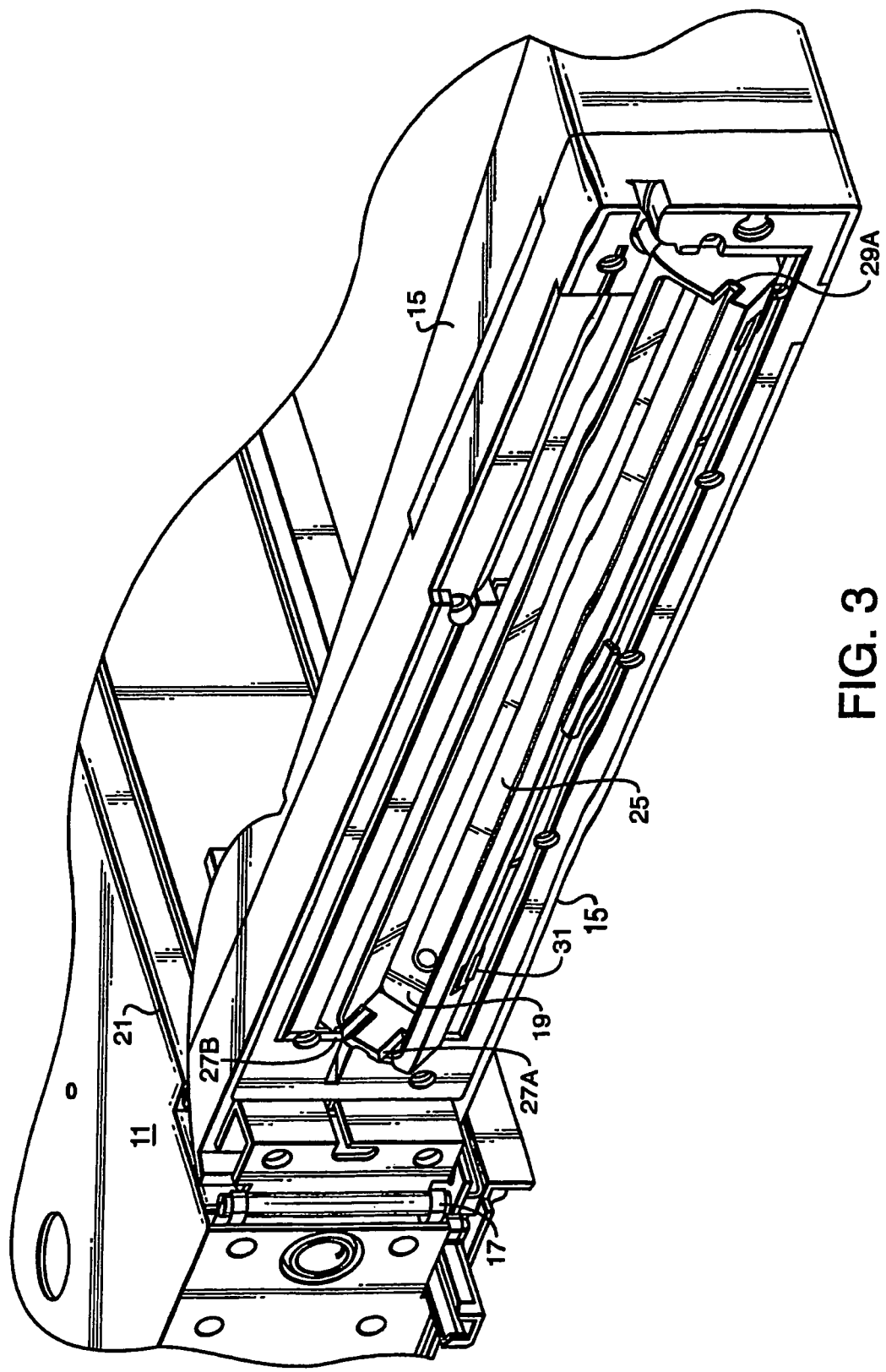
FIG. 3 depicts a device embodying features of the present invention.

Housing 15 has a chamber 19 for receiving one or more columns or cartridges (not shown) as best seen in FIG. 3. Columns and cartridges are well known in the art. Columns and cartridges generally have an inlet for receiving fluid and an outlet for discharging fluid and an column axis corresponding generally with the flow of fluid from the inlet to the outlet. The columns and cartridges are suitable for performing separations in which a constant temperature is desirable.

For the purpose of this discussion, the column and/or cartridge inlet will be described as being close to the positioning means 17. And, the column and/or cartridge outlet will be described as being distal from the positioning means 17.

Positioning means 17 places the column and cartridge outlet in proximity to a detector (not shown). As used herein the term "detector" means any instrument which produces a distinctive signal in the presence of a composition. The detector is preferably selected from the group of detectors consisting of mass spectrometers; optical detectors, such as photodiode array detectors, ramon light scattering detectors, absorbance detectors, fluorescence detectors, refractometers, electrochemical detectors, viscosity detectors and the like. It is common to place mass spectrometers to the right of a pump and sample injector assembly, as one faces the front of the pump and sample injector assembly.

Preferably, the columns and cartridges receive sample from a sample injector and a fluid from a pump. A common sample injector is an autosampler. An autosampler is a apparatus for receiving samples in one or more vials or containment vessels and withdrawing aliquots of such samples. The aliquots are injected into the flow from a pump in an automatic manner. This application will use the term sample injector to encompass manual sample injectors and automatic sample injectors, i.e. autosamplers.

The positioning means 17 comprises an arm, slide, linkage, intermitting sliding elements, such as sliding cylinders in the nature of a telescope, flexible conduit members or hinges. Positioning means 17 depicted in FIGS. 1 and 2, is a hinge which secures the housing to a pump or sample injector designated by the numeral 21. Starting with FIG. 1, positioning means 17 allows the housing 15 to swing outward and, moving to FIG. 2, extend to the right to assume a position in from of a detector (not shown) placed to the right The arm, slide, linkage, intermitting sliding elements, flexible conduit members or hinge are capable of movement and positioning to allow the housing 15 to be placed with the outlet of a column or cartridge proximal to the inlet of the detector. The short distance spanning the outlet of the column and/or cartridge to the inlet of the detector is, preferably, spanned by a relatively short tube or conduit. The shorter distance improves the sensitivity of the detector, pump and sample injector combination by reducing band spreading. For example, in one embodiment where the positioning means 17 comprises a hinge, the hinge is affixed to the pump or sample injector apparatus 21 and the housing is swung to a position in which the outlet of the column is close to the inlet of the detector.

Other embodiments of positioning means 17, such as arm, slide, linkage, interfitting sliding elements, flexible conduit members and the like, are well known. Thus, one end of an arm, slide, linkage, interfitting sliding elements, flexible conduit member or similar element would be attached to the pump or sample injector 21 and the other end made available for movement to a position proximal to the inlet of a detector.

Preferably the housing 15 has a cradle 23. The cradle 23 is rotatably attached to the housing 15 with a cradle axis of rotation substantially aligned parallel with the column axis. The cradle 23 has a cradle opening 25 for receiving columns and cartridges (not shown). The cradle opening 25 has an open position, depicted in FIG. 3 and a closed position, depicted in FIG. 2. The cradle opening 25 is shut upon the cradle 23 assuming the closed position to provide a temperature controlled environment for the column or cartridge. In the open position, the cradle opening 25 is accessible to receive and remove columns and cartridges.

Cradle 23 has slots 27a and 27b for receiving one or more tubes or conduits for placing fluid into a column or cartridge. Cradle 23 also has one or more slots 29a (only one shown) for receiving one or more tubes or conduits for removing fluid from the column or cartridge and directing such fluid into the inlet of a detector.

Housing 15 further comprises a heating element 21 for maintaining the chamber 19 and with greater particularity the cradle opening 25 at a constant temperature. As best seen in FIG. 3, the heating element 21 is contained in the cradle 23. One preferred heating element 21 is electrical resistance circuits thermostatically controlled in a manner known in the art.

Preferably, device 11 is part of an assembly 21 of a pump, sample injector or combined modules of pumps and sample injector. Thus, the device of the present invention is convenient for use and promotes laboratory bench organization. The method of the present invention will be described with respect to the operation of the device. The invention features a method of minimizing band spreading in separation processes.

The method comprising the steps of providing a housing 15 having a chamber 19 for receiving one or more columns or cartridges. The columns and cartridges have an inlet for receiving fluid and an outlet for discharging fluid and an column axis corresponding generally with the flow of fluid from the inlet to the outlet. The column and cartridges are for performing separations such as liquid chromatography. The housing has a heating element 31 for maintaining the chamber 19 at a constant temperature. The method further comprises the step of providing positioning means 17 for placing the column and cartridge outlet in proximity to a detector to allow connection to a detector. The method comprises the step of placing the housing 15 in proximity to the detector with the positioning means 17 to minimize tubing spanning from the column outlet to the detector and minimize band spreading.

Preferably, the method further comprises the step of providing a device 11 wherein the housing 15 has a cradle 23 having a cradle opening 25. The cradle 23 has a cradle axis of rotation substantially aligned parallel with the column axis. The cradle 23 rotates between an open position and a closed position. In the open position, the cradle opening is accessible for receiving columns and cartridges. The cradle opening 25 is shut upon the cradle 23 assuming the closed position to provide a controlled environment for the column and/or cartridge. The method further comprising the steps of rotating the cradle 23 to the open position to receive a column or cartridge. Next, rotating the cradle 23 to assume the closed position, and positioning the column or cartridge in proximity to the detector.

Thus, the present invention has been described in a manner which enables the individual skilled in the art to make and use the invention. These and other features and advantages will be apparent to individuals skilled in the art upon reference to the figures and detailed description that follow.

The invention claimed is:

1. A device for moving a chromatography column proximate to a detector, comprising:
   a housing comprising:
      a chamber configured to receive a column for performing a chromatography separation, the column having an inlet to receive a fluid and an outlet for discharging the fluid; and
      a heating element for maintaining the chamber at a constant temperature; and
   a positioning mechanism coupled to the housing and adapted for attachment to a chromatography system component, the positioning mechanism configured to move the housing between a first position at which the column is proximate to the chromatography system component and a second position at which the outlet of the column is proximate to a detector.

2. The device of claim 1 wherein the detector is selected from the group of detectors consisting of mass spectrometers; optical detectors, such as photodiode array detectors, ramon light scattering detectors, absorbance detectors, fluorescence detectors, refractometers, electro-chemical detectors and viscosity detectors.

3. The device of claim 1 wherein the housing has a cradle having a cradle axis of rotation configured to be parallel to an axis of the column, the cradle being rotatable between an open position for accessing the column when held in the cradle and a closed position.

4. The device of claim 3 wherein the heating element is disposed in the cradle.

5. The device of claim 4 wherein the heating element comprises an electrical resistance heater.

6. The device of claim 1 wherein the chromatography system component is a pump.

7. The device of claim 1 wherein the chromatography system component is a sample injector.

8. The device of claim 1 wherein the positioning mechanism comprises a hinge configured to rotate the housing about a hinge axis.

9. The device of claim 1 wherein the positioning mechanism comprises a sliding element.

10. The device of claim 1 wherein the positioning mechanism comprises a flexible conduit configured for coupling to the inlet of the column.

* * * * *